Figure 1:
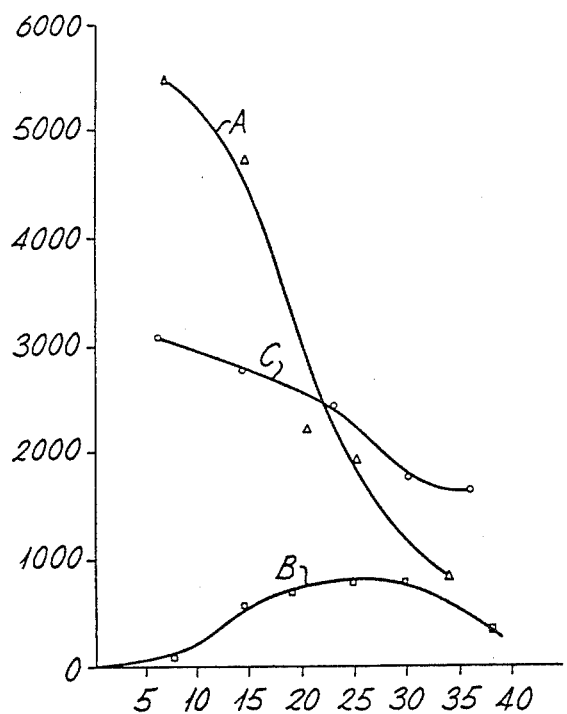

United States Patent [19]

Causton et al.

[11] Patent Number: 4,732,617
[45] Date of Patent: Mar. 22, 1988

[54] FLUORIDE-CONTAINING COMPOSITIONS

[75] Inventors: Brian E. Causton, Basingstoke; Alfiati N. T. Thuy, Wentworth, both of England

[73] Assignee: National Research Development Corporation

[21] Appl. No.: 910,669

[22] Filed: Sep. 23, 1986

Related U.S. Application Data

[63] Continuation of Ser. No. 738,689, May 28, 1985, abandoned, which is a continuation of Ser. No. 524,153, Aug. 18, 1983, abandoned.

[30] Foreign Application Priority Data

Aug. 24, 1982 [GB] United Kingdom ............... 8224265

[51] Int. Cl.$^4$ ............................................. C09K 3/00
[52] U.S. Cl. .................................... 106/35; 424/52; 433/217.1
[58] Field of Search ................. 424/52; 433/217; 106/35

[56] References Cited

U.S. PATENT DOCUMENTS

| | | | |
|---|---|---|---|
| 3,520,849 | 7/1970 | Vandenberg | 528/244 |
| 3,882,600 | 5/1975 | Plymale | 32/15 |
| 4,259,117 | 3/1981 | Yamauchi et al. | 106/35 |
| 4,427,652 | 1/1984 | Gaffar | 424/52 |

FOREIGN PATENT DOCUMENTS

| | | |
|---|---|---|
| 7900456 | 7/1979 | European Pat. Off. . |
| 1965046 | 7/1971 | Fed. Rep. of Germany . |
| 3024944 | 2/1982 | Fed. Rep. of Germany . |
| 1172892 | 2/1959 | France . |
| 1090249 | 11/1967 | United Kingdom . |
| 1372199 | 10/1974 | United Kingdom . |
| 1511614 | 5/1978 | United Kingdom . |
| 1551388 | 8/1979 | United Kingdom . |
| 2083354 | 3/1982 | United Kingdom . |
| 2090265 | 7/1982 | United Kingdom . |

Primary Examiner—Amelia Burgess Yarbrough
Attorney, Agent, or Firm—Jacobs & Jacobs

[57] ABSTRACT

A composition comprising fluoride ion and a polymer which is permselective to fluoride ion is provided for dental prophylaxis or therapy. The composition may be formulated as a gel, for example in a toothpaste; as a dentifrice; or as a mouthwash.

12 Claims, 4 Drawing Figures

FLUORIDE-CONTAINING COMPOSITIONS

This is a continuation of Ser. No. 738,689 filed May 28, 1985, abandoned, which is a continuation of Ser. No. 524,153, filed Aug. 18, 1983, now abandoned.

This invention relates to fluoride-containing compositions; more particularly, this invention relates to fluoride-containing compositions for use in dental prophylaxis and therapy.

Compositions comprising fluoride ions occupy an important place in preventative dentistry: fluoride ions have both a systemic and topical benefit to teeth. The latter can be obtained either by the addition of a fluoride, such as sodium fluoride, to the central water supply or from the deliberate topical application of solutions, gels or pastes. Gels are preferred to solutions since they can more easily be kept in contact with the teeth for the required time.

The prophylatic and therapeutic use of acidulated phosphate fluoride (APF) gels to strenghten and restore dental enamel against acid attack has been common for two decades (Wellock and Brudevold: Arch. Oral Biol. 8, pages 179–182, 1963). APF gels typically comprise a cellulose derivative, soddium fluoride, hydrofluoric acid and sodium phosphate and have a fluoride concentration of about 20,000 ppm.

However, one teaspoonful of such a gel is acutely toxic to a 20 kg child and three-quarters of a cup of such a gel constitutes a lethal dose of fluoride. In consequence, treatment has to be effected by the dental practitioner to avoid accidental fluorosis.

This invention, in one aspect, seeks to provide fluoride prophylaxis or therapy in dentistry utilising fluoride concentrations which will obviate, or make much less possible, accidental fluorosis. In another aspect, this invention seeks to provide more effective fluoride prophylaxis or therapy utilising conventional fluoride concentrations.

According to the present invention, there is provided a polymer which is permselective with respect to fluoride ion and which comprises both hydrophobic groups and backbone phosphate groups for use in dental prophylaxis or therapy. Particularly important dental prophylaxis or therapy includes use in reduction of dental caries and use in enhancing the resistance of dental enamel to acid attack.

One important class of polymer which has proved valuable in the performance of the invention comprises the saturated or unsaturated, substituted or unsubstituted poly(organo phosphate)s. Preferably, the polymer comprises a substituted or unsubstituted poly(cycloalkylene phosphate), especially a substituted or unsubstituted poly(cyclohexylene phosphate). The preferred polymer has the formula:

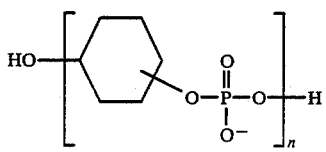

wherein n represents a number greater than two, typically from 10 to 100, preferably from 25 to 60. The formula acknowledges that a mixture of isomers, including stereoisomers, may be present. Poly(1,2-cyclohexylene phosphate) is the particularly preferred polymer.

The number average molecular weight of the polymer may be from 2,000 to 20,000 or more, preferably from 5,000 to 10,000.

These polymers are known per se; they may be prepared by analogy with the process disclosed in French Patent No. 1172892 or by the process disclosed in U.S. Pat. No. 3,520,849. For completeness, however, Example 1 describes a preparation.

Desirably, the polymers used in this invention are cross-linked with a minor amount (typically no more than 10 wt%, preferably less than 5 wt%) of a cross-linking monomer. This may be a polyhydroxy compound of functionality greater than 2; for example, glycerol or pentaerythritol or a tris-(or higher) phosphate compound; for example, phytic acid, or a precursor thereof such as an acid chloride or anhydride. Free radical cross-linking may be utilised, for example by copolymerising a minor amount of an ethylenically unsaturated moiety; and then polymerising these moieties in a manner known per se. Examples of such moieties include allyloxypropyldiol and hydroxyethyl methacrylate (HEMA).

Polymers useful in the performance of this invention should be layer forming polymers; should be capable of binding fluoride ion; should have calcium salts which are insoluble in slightly alkaline media, such as oral fluids; they should not etch dental enamel in the presencee of fluoride ion; they, and any decomposition products, should be non-toxic at the concentrations administered. This is the case with the above-mentioned polymers.

In accordance with a further aspect of this invention, there is provided a composition comprising:

(i) a polymer which is permselective with respect to fluoride ion and which comprises both hydrophobic groups and backbone phosphate groups; and (ii) a source of fluoride ion.

By "backbone phosphate group" is meant herein a phosphate group which is linked by a plurality of covalent bonds to the polymer network (in contra distinction to a pendant phosphate group which is linked by a single covalent bond to the polymer network).

By "permselective with respect to fluoride ion" is meant herein that a layer of the subject polymer acts as a semi-permeable membrane with respect to fluoride ion.

By "source of fluoride ion" is meant herein any species which can, in the presence of aqueous media and a permselective polymer as aforesaid, present fluoride ion to dental enamel. Examples include a fluoride complex such as one comprising the $AlF_6^{-3}$ anion; a fluoride of a transition metal of Groups IVA or VIII such as $ZrF_4$, $FeF_3$; a fluoride of a metal of Group IVB, namely $SnF_2$ and $PbF_2$; and a bifluoride such as $KHF_2$. A preferred source of fluoride ion comprises an alkali metal fluoride, such as sodium fluoride.

Compositions of the invention may comprise fluoride concentrations typically greater than 5,000 ppm; for example up to 10,000 ppm or even up to 25,000 ppm. Such compositions would have to be administered by the dental practitioner but would provide more effective fluoride propylaxis or therapy than conventional APF compositions. More preferably, however, compositions of the invention comprise fluoride concentrations of 5,000 ppm or less; for example less than 2,500 ppm, preferably less than 1,000 ppm. Compositions comprising as little as 500 to 800 ppm fluoride have been found to give useful effects.

The compositions of this invention may be dissolved in aqueous media, for example to provide a mouthwash, which may also comprise a disinfectant. Preferably, however, they are formulated as a gel which may be incorporated in a dentrifrice or a toothpaste. The gel may comprise a conventional thickening agent such as an alginate, carboxymethyl cellulose or poly(N-vinyl pyrrolidone).

The following Examples illustrate the invention:

EXAMPLE 1

This Example describes the preparation of poly(cyclohexyl ethylphosphate).

11.61 g (0.1 mole) of 1,2-cyclohexane diol was dissolved in 13.8 g (0.1 mole) of diethyl phosphite in a round bottom flask with a Claisen head having a downward condenser and a receiver for distillation. 0.05 g of sodium was then dissolved in a small amount of ethanol and the alcoholic sodium ethoxide so formed was added to the mixture.

The mixture was next heated to 170° C. under a stream of dry nitrogen and the transesterified ethanol was collected (70% of expected amount). The remaining product was then incorporated in a high vacuum line and maintained at 170° C. for 2 days when a yellow solid was obtained. This was the corresponding polyphosphite of the formula:

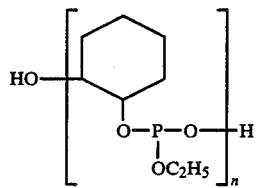

The polyphosphite was then oxidised by dissolution in a solution of $N_2O_4$ in dimethyl formamide (formed by bubbing $NO_2$ into dimethyl formamide until a green-brown solution was obtained), excess $N_2O_4$ being removed by passing nitrogen through the solution. Finally, the dimethyl formamide was removed by vacuum distillation and the remaining polymer cleaned by dissolution in methanol and precipitation by diethyl ether.

EXAMPLE 2

In this Example three solutions were utilised:
(A) a commercial APF solution ("ALPHAGEL" ex AD International Ltd.), as received, comprising 15,000 ppm $F^-$(comparative);
(B) an aqueous solution comprising 0.5 wt% poly(cyclohexylene ethylphosphate) and 10 ppm $F^-$, as sodium fluoride; and
(C) an aqueous solution comprising 0.5 wt% poly(cyclohexylene ethylphosphate) and 1 wt% sodium fluoride (about 4,500 ppm $F^-$).

Three sets of 5 molar teeth (all 8 s) were painted with nail varnish (10% polystyrene in ethylacetate) so that each tooth in each set retained an unvarnished area 3 mm×4 mm of exposed enamel. All of the painted teeth in a given set wer then immersed in one of the three solutions supra for 24 hours at 25° C. The resulting fluoridated teeth were removed; washed with distilled water; dried; and weighed. Each fluorinated tooth was next immersed in a separate 1 ml aliquot of 2N perchloric acid for 10 minutes at 25° C. The resulting etched tooth was removed; washed with distilled water; dried; and weighed. The aliquot of perchloric acid and the washings were analysed for fluoride content by the method of Weatherall and Hargreaves (Arch. Oral Biol. 10, pages 139-142, 1965). The etching and weighing procedure was repeated 10 times for each tooth thereby enabling the estimation of the fluoride content of the enamel at several depths. Finally, the nail varnish was removed and the etching and weighing procedure repeated for the unfluoridated enamel.

FIG. 1 of the accompanying drawings illustrates graphically the observed variation of fluoride concentration, as ordinate, (ppm $F^-$) against enamel depth, as abscissa, (as $g.cm^{-2}\times 10^{-2}$).

From the Figure, it can be seen that the two solutions (A and C) containing high fluoride concentrations also create high fluoride concentrations in the enamel surface, but that this fluoride concentration decreases with enamel depth. The decrease with enamel depth is greater in the case of immersion in solution A than in the case of immersion in solution C. At enamel depths greater than 25 $g.cm^{-2}\times 10^{-2}$ the fluoride concentration is greater in the case of immersion in solution C than in the case of immersion in solution A. The solution B containing low fluoride concentration, however, creates an increased concentration of fluoride with increasing enamel depth such that at enamel depths of 30 to 35 $g.cm^{-2}\times 10^{-2}$ there is no significant difference in fluoride concentration between the case of immersion in solution A and solution B.

EXAMPLE 3

In this Example eight solutions were utilised:
(A) as in Example 2 (comparative);
(D) an aqueous solution comprising 0.1 wt% poly(cyclohexylene ethylphosphate) and 10 ppm $F^-$, as sodium fluoride;
(E) an aqueous solution comprising 0.1 wt% poly(cyclohexylene ethylphosphate) and 50 ppm $F^-$, as sodium fluoride;
(F) an aqueous solution comprising 0.1 wt% poly(cyclohexylene ethylphosphate) and 100 ppm $F^-$, as sodium fluoride;
(G) an aqueous solution comprising 0.1 wt% poly(cyclohexylene ethylphosphate) and 200 ppm $F^-$, as sodium fluoride;
(H) an aqueous solution comprising 0.1 wt% poly(cyclohexylene ethylphosphate) and 500 ppm $F^-$, as sodium fluoride;
(I) an aqueous solution comprising 0.1 wt% poly(cyclohexylene ethylphosphate) and 5,000 ppm $F^-$, as sodium fluoride;
(J) an aqueous solution comprising 0.1 wt% poly(cyclohexylene ethylphosphate) and 10,000 ppm $F^-$, as sodium fluoride.

Eight sets of 5 teeth (all 8 s) were painted with nail varnish and all of the teeth in a given set were immersed in one of eight solutions supra essentially as in Example 2 except that the time of immersion was 15 minutes at 25° C. The resulting fluoridated teeth were removed; washed with distilled water; dried; and weighed. Each fluoridated tooth was then immersed in a separate aliquot Tyrodes solution for 24 hours at 25° C., the solution being changed hourly. Each tooth so treated was next etched and estimated for fluoride as in Example 2.

Tyrodes solution has the composition:

| component | g liter$^{-1}$ |
|---|---|
| CaCl$_2$ | 0.200 |
| KCl | 0.200 |
| MgCl$_2$ 6H$_2$O | 0.05 |
| NaCl | 8.00 |
| NaHCO$_3$ | 1.00 |
| NaH$_2$PO$_4$ H$_2$O | 0.05 |
| Glucose | 1.00 |

Figure 2:
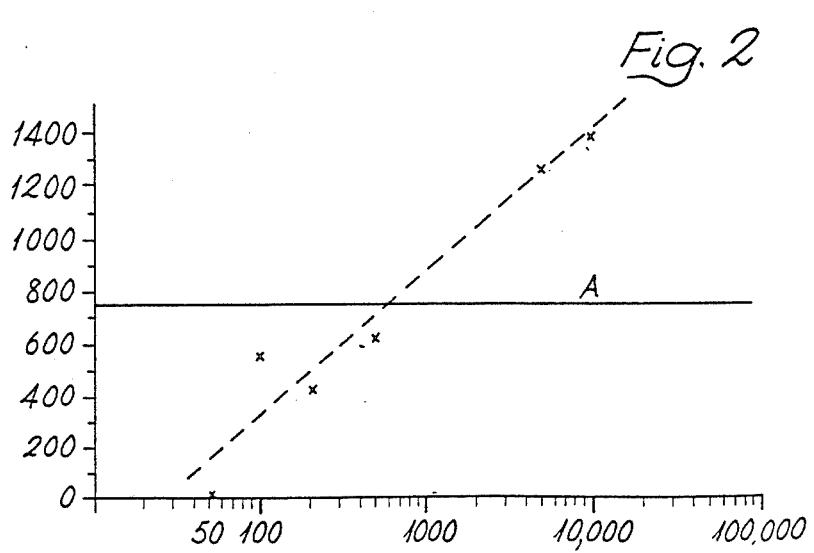

FIG. 2 of the accompanying drawings illustrates graphically, on a logarithmic scale, the observed variation of retained fluoride concentration, as ordinate, (ppm F$^-$) against fluoride concentration in the immersion solution, as abscissa, (ppm F$^-$).

From the Figure, it can be seen that the fluoride concentration retained by teeth treated with solution A was that expected for teeth treated with an aqueous solution comprising 0.1 wt% poly(cyclohexylene ethylphosphate) and 800 ppm F$^-$, as sodium fluoride. It is also observed that an aqueous solution comprising 0.1 wt% poly(cyclohexylene ethylphosphate) and 100 ppm F$^-$, as sodium fluoride gave a fluoride concentration retained by teeth of 550 ppm: comparison with solution A shows that a 150 times reduction in F$^-$ content of the solutions of the invention gives only a 30% rduction in fluoride concentration retained by the teeth.

EXAMPLE 4

Eight sets of 5 teeth (all 8 s) were painted with nail varnish and all of the teeth in a given set were immersed for 15 minutes at 25° C. in one of the eight solutions used in Example 3. The calcium content of each solution was then determined using a Ca$^{+2}$ electrode.

Figure 3:
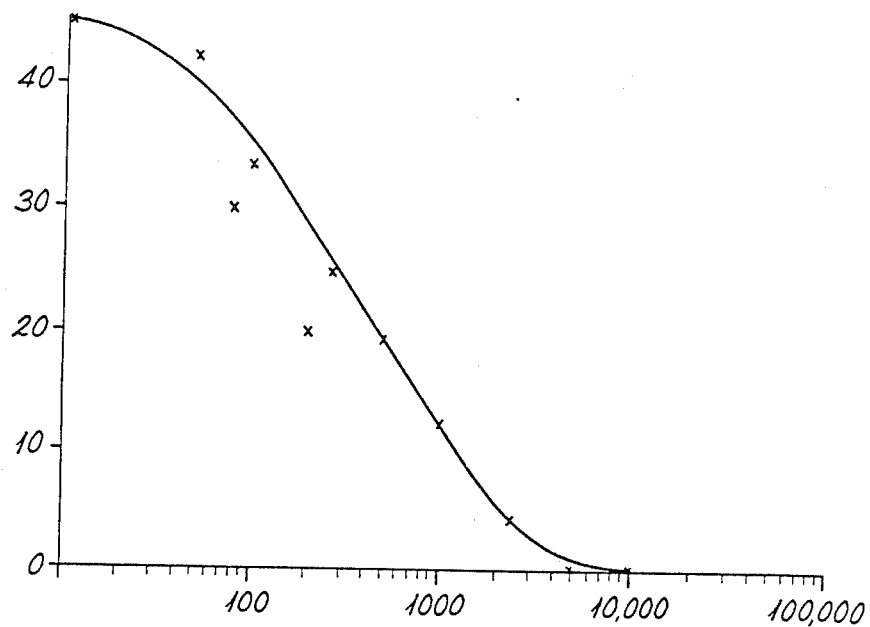

FIG. 3 of the accompanying drawings illustrates graphically on a logarithmic scale, the observed variation in solution calcium concentration, as ordinate, (M Ca$^{+2}$)/cm$^2 \times 10^{-4}$) againt fluoride concentration in the immersion solution, as abscissa, (ppm F$^-$).

From the Figure, it can be seen that at about 100 ppm F$^-$ there is a pronounced change of curve gradient with dissolved calcium content decreasing rapidly with increasing fluoride concentrations.

EXAMPLE 5

Eight sets of 5 teeth (all 8 s) were painted with nail varnish so that each tooth in each set retained two unvarnished areas, each 4 mm $\times$ 3 mm, of exposed enamel. All of the painted teeth in a given set then had one (but not the other, which acted as control) of the unvarnished areas contacted for 15 minutes at 25° C. with one of the eight solutions used in Example 3. Each unvarnished area on a given tooth was contacted for 30 minutes with separate aliquots of acetate buffer (pH=4.5). The aliquots were analysed for Ca$^{+2}$ using a Ca$^{+2}$ eletrode.

Figure 4:
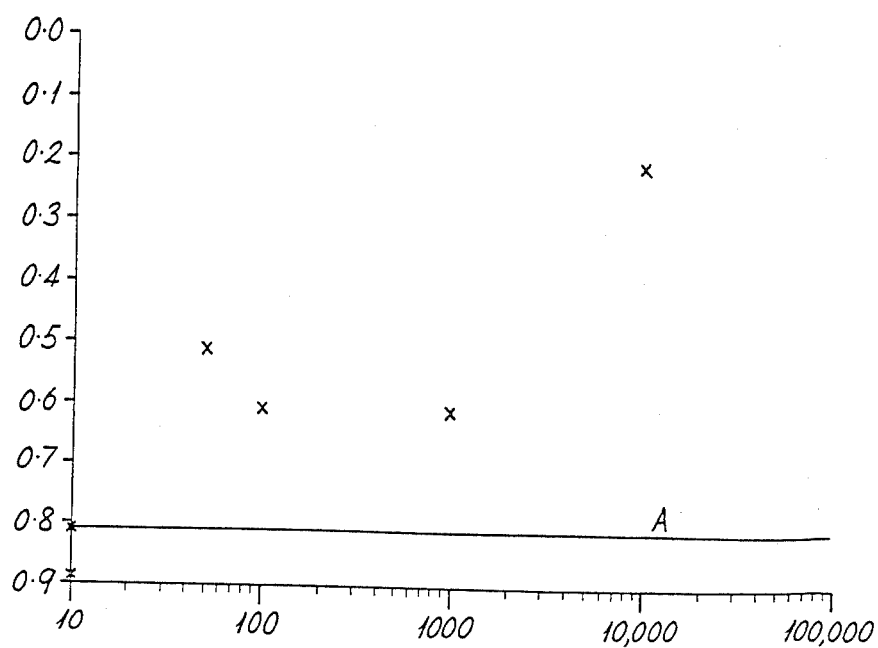

FIG. 4 of the accompanying drawings illustrates graphically, on a logarithmic scale, the observed variation in solution calcium concentration, as ordinate, ([Ca$^{+2}$] test/[Ca$^{+2}$] control) against fluoride concentration in the immersion solution, as abscissa, (ppm F$^-$).

From the Figure, it can be seen that the enamel is about 65% less soluble when treated with the solution of the invention. Solution A, despite its very high fluoride concentration, renders enamel treated therewith only 19% less soluble.

It will be seen that the compositions of this invention provide both an enhanced sub-surface uptake of fluoride and an enhanced retention of fluoride by dental enamel, for a given fluoride concentration, relative to conventional APF compositions. The compositions of this invention also provide enhanced acid resistance in treated dental enamel, relative to conventional APF compositions.

What is claimed is:

1. An anti-caries composition for dental prophylaxis, which comprises poly(1,2-cyclohexylene phosphate) having a number average molecular weight of from 2,000 to 20,000, and an anti-caries effective amount of sodium fluoride.

2. A composition according to claim 1, wherein said sodium fluoride comprises less than 1,000 ppm of the composition.

3. A composition according to claim 1, in liquid form, wherein said polymer and said source of fluoride ion are dissolved in water.

4. An aqueous solution for use in dental prophylaxis and therapy, which comprises 0.1 wt. % poly(1,2-cyclohexylene phosphate) and 10–1000 ppmF$^-$ as sodium fluoride.

5. An anti-caries composition for dental prophylaxis, which comprises a substituted or unsubstituted poly(1,2-cycloalkylene phosphate) and an anti-caries effective amount of a source of fluoride ion.

6. A composition according to claim 3, wherein said polymer comprises a substituted or unsubstituted poly(1,2-cyclohexylene phosphate).

7. A composition according to claim 5, wherein the source of fluoride ion comprises a fluoride complex; a fluoride of a transition metal of Groups IVA or VIII; a fluoride of a metal of Group IVB; or an alkali metal fluoride.

8. A composition according to claim 5 wherein the source of fluoride ion comprises sodium fluoride.

9. A composition according to claim 5 wherein the source of fluoride ion comprises up to 25,000 ppm (as F$^-$) of the composition.

10. A composition according to claim 9 wherein the source of fluoride ion comprises up to 10,000 ppm (as F$^-$) of the composition.

11. A composition according to claim 9 wherein the source of fluoride ion comprises less than 2,500 ppm (as F$^-$) of the composition.

12. A composition according to claim 9 wherein the source of fluoride ion comprises less than 1,000 ppm (as F$^-$) of the composition.

* * * * *